(12) United States Patent
Bhambri

(10) Patent No.: US 7,892,369 B2
(45) Date of Patent: Feb. 22, 2011

(54) METHOD OF MODIFYING THE MICROSTRUCTURE OF TITANIUM ALLOYS FOR MANUFACTURING ORTHOPEDIC PROSTHESES AND THE PRODUCTS THEREOF

(75) Inventor: Shushil K. Bhambri, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 332 days.

(21) Appl. No.: 11/737,515

(22) Filed: Apr. 19, 2007

(65) Prior Publication Data

US 2007/0251614 A1    Nov. 1, 2007

Related U.S. Application Data

(60) Provisional application No. 60/745,917, filed on Apr. 28, 2006.

(51) Int. Cl.
*C22F 1/18* (2006.01)
*C22C 14/00* (2006.01)

(52) U.S. Cl. .................................. 148/669; 148/421

(58) Field of Classification Search ............... 148/421, 148/669
See application file for complete search history.

(56) References Cited

U.S. PATENT DOCUMENTS

| | | | |
|---|---|---|---|
| 3,492,172 A | 1/1970 | Sauvageot et al. |
| 3,901,743 A | 8/1975 | Sprague et al. |
| 4,053,330 A | 10/1977 | Henricks et al. |
| 4,505,764 A | 3/1985 | Smickley et al. |
| 4,536,234 A | 8/1985 | Eylon et al. |
| 4,624,714 A | 11/1986 | Smickley et al. |
| 4,854,977 A | 8/1989 | Alheritiere et al. |
| 4,878,966 A | 11/1989 | Alheritiere et al. |
| 5,125,986 A | 6/1992 | Kimura et al. |
| 2002/0179208 A1 | 12/2002 | Lin et al. |
| 2005/0257864 A1 | 11/2005 | Marquardt et al. |

(Continued)

FOREIGN PATENT DOCUMENTS

EP    0921207 A1    6/1999

(Continued)

OTHER PUBLICATIONS

Qazi et al., Effects of Thermal Treatment on the Mechanical Properties of Biomedical Titanium Alloys, Sep. 8, 2003, ASM International, p. 1-8.*

(Continued)

*Primary Examiner*—Roy King
*Assistant Examiner*—Caitlin Fogarty
(74) *Attorney, Agent, or Firm*—Baker & Daniels LLP

(57) ABSTRACT

A titanium alloy subjected to thermal treatment followed by quenching. The thermal treatment raises the temperature of the alloy to a temperature above the alloy's recrystallization temperature and below the alloy's beta-transus temperature to cause a phase shift within the alloy. After the thermal treatment has been applied for a predetermined time, the alloy is rapidly quenched, preserving the phase shift induced by the thermal treatment. By the present method, the microstructure of the titanium alloy is changed from a fine grained alpha-beta phase to a microstructure substantially comprised of an equiaxed alpha phase and an acicular or plate-like alpha phase. The resulting prostheses may have a microstructure including between 25% and 75% percent acicular alpha phase, for example.

16 Claims, 6 Drawing Sheets

U.S. PATENT DOCUMENTS

2005/0284549 A1 12/2005 Woodfield et al.
2006/0225821 A1 10/2006 Ninomiya

FOREIGN PATENT DOCUMENTS

| JP | 60/086256 | 5/1985 |
|---|---|---|
| JP | 62-205253 | 9/1987 |
| JP | 03-170649 | 7/1991 |
| JP | 06-200305 | 7/1994 |

OTHER PUBLICATIONS

Gilbert et al., Heat Treating of Titanium and Titanium Alloys-Furnace Equipment and Accessories, 1991, ASM International, ASM Handbook, vol. 4, 10th Edition, p. 1-3.*

The European Search Report and Opinion mailed Sep. 8, 2008, from the European Patent Office in related European Application No. EP07008493.4.

Rack et al. "Titanium alloys for biomedical applications" Materials Science and Engineering, Elsevier Science S.A., CH, vol. 26, No. 8, Oct. 12, 2005, pp. 1269-1277.

Imam M.A. Fatigue and Microstructural Properties of Quenched Ti-6Al-4V Metallurgical Transactions, vol. 14A, Feb. 1, 1983, pp. 233-240.

Bhasin, S.S., et al. "Studies in titanium-based ental implant material" Ceramic Engineering and Science Proceedings, vol. 24, No. 3, 2003, pp. 245-254.

Hickey et al. "Heat Treatment Effects on the Mechanical Properties in Ti-6Al-6V-2Sn", Journal of Testing and Evaluation, vol. 1, No. 2, Jan. 1, 1900, pp. 166-169.

The Canadian Office Action mailed Sep. 30, 2009 in related Canadian Application No. 2,585,908.

* cited by examiner

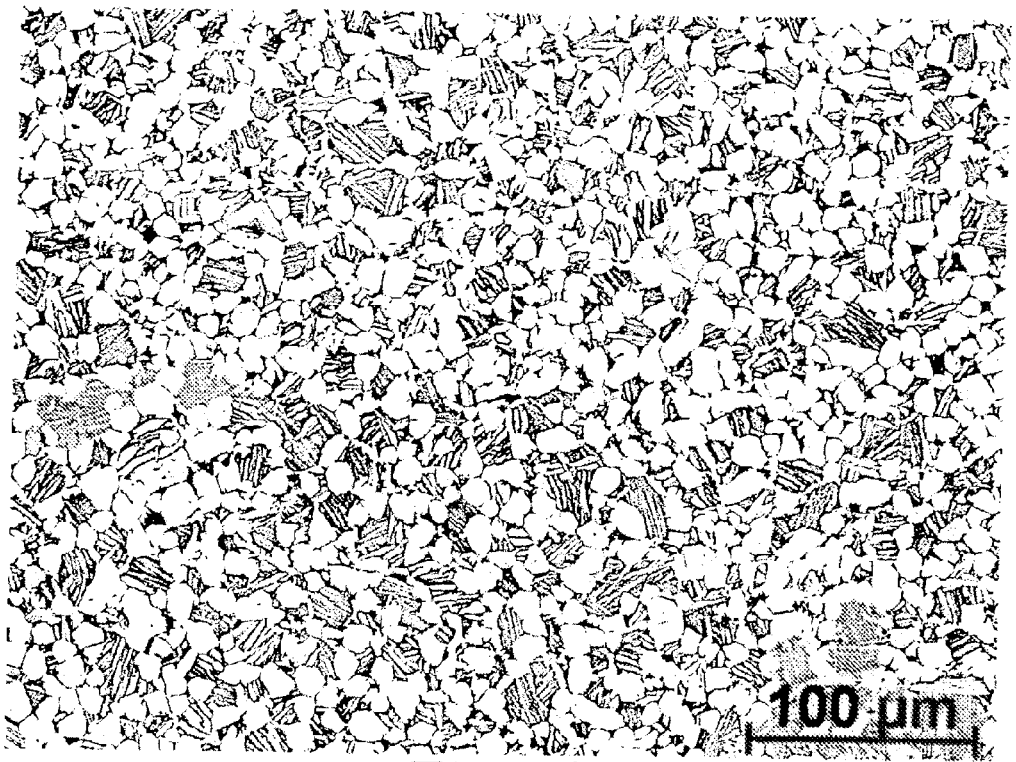
FIG_4
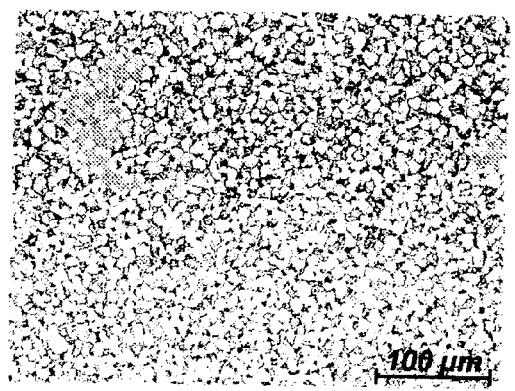
FIG_5

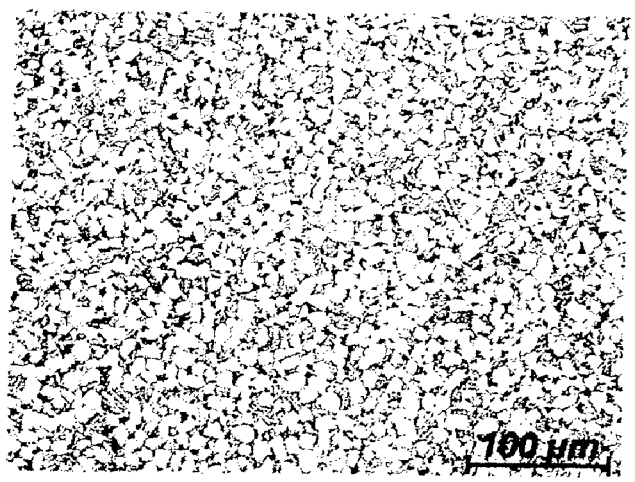
FIG_6
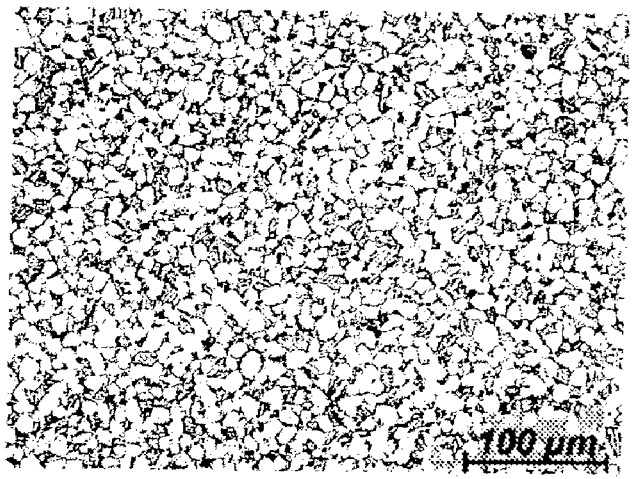
FIG_7
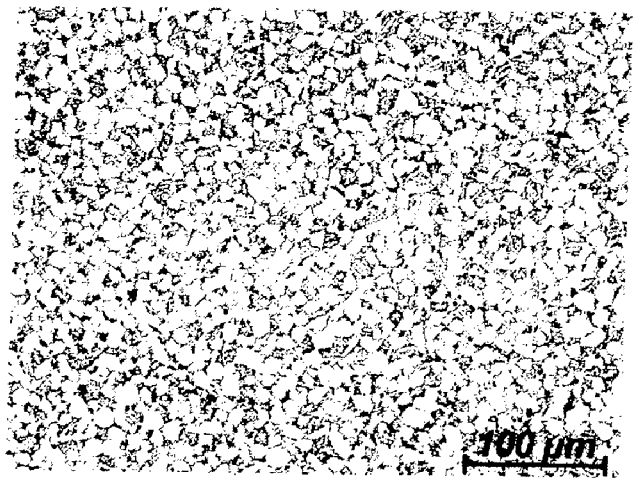
FIG_8

METHOD OF MODIFYING THE MICROSTRUCTURE OF TITANIUM ALLOYS FOR MANUFACTURING ORTHOPEDIC PROSTHESES AND THE PRODUCTS THEREOF

CROSS-REFERENCE TO RELATED APPLICATIONS

This application claims the benefit under Title 35, U.S.C. §119(e) of U.S. Provisional Patent Application Ser. No. 60/745,917, entitled Method of Modifying the Microstructure of Titanium Alloys for Manufacturing Orthopedic Prostheses and the Products Thereof, filed on Apr. 28, 2006, the disclosure of which is expressly incorporated herein by reference.

BACKGROUND OF THE INVENTION

1. Field of the Invention

The present invention relates to a method for modifying the microstructure of titanium alloys for use in manufacturing orthopedic prostheses, and orthopedic prostheses made from such method.

2. Description of the Related Art

Orthopedic prostheses are used to replace or repair damaged or diseased bone in a patient's body. To construct an orthopedic prosthesis, titanium alloys, such as Ti-6Al-4V for example, may be used which incorporate the superior strength to weight ratio of titanium. Additionally, some prostheses are manufactured to be modular, i.e., two or more components are individually manufactured and are then connected to form a complete prosthesis, such as, for example, a hip stem comprised of a separate stem section and neck section connected via a Morse taper.

What is needed is a titanium alloy which is an improvement over the foregoing.

SUMMARY OF THE INVENTION

The present invention provides a method for modifying the microstructure of titanium alloys for use in the manufacture of orthopedic prostheses, and orthopedic prostheses made from such method. In one embodiment, an orthopedic prosthesis is initially formed from titanium alloy and is subsequently subjected to thermal treatment followed by quenching. The thermal treatment raises the temperature of the alloy to a hold temperature above the alloy's recrystallization temperature and below the alloy's beta-transus temperature to cause a phase shift within the alloy. After the thermal treatment has been applied for a predetermined hold time, the alloy is rapidly quenched, preserving the phase shift induced by the thermal treatment. By the present method, the microstructure of the titanium alloy is changed from a fine grained alpha-beta phase to a microstructure substantially comprised of an equiaxed alpha phase and an acicular or plate-like alpha phase. In another embodiment, an alloy is initially subjected to the present method and then subsequently formed into a prosthesis. The resulting prostheses may have a microstructure including between 25% and 75% percent acicular alpha phase, for example.

Advantageously, titanium prostheses exhibiting the present microstructure have improved resistance to fretting fatigue. Additionally, the present method allows for the entire prosthesis, as opposed to an individual section, to be subjected to the microstructural modification and allows for the prosthesis to be post-processed, i.e., additional properties changes can be imparted to the surface of the prosthesis, such as by cold working.

In one form thereof, the present invention provides a method for modifying the microstructure of titanium alloys including the steps of: heating a titanium alloy to a maximum temperature above the alloy's recrystallization temperature and below the alloy's beta-transus temperature; holding the alloy at the maximum temperature; and quenching the titanium alloy.

In another form thereof, the present invention provides an orthopedic prosthesis including: a titanium alloy having a microstructure including an acicular alpha phase of between 20% and 75% of the area of a micrograph of said microstructure taken at 250× magnification.

In yet another form thereof, the present invention provides a method for modifying the microstructure of titanium alloys including the steps of: heating a titanium alloy to a maximum temperature between 1675° F. and 1775° F.; holding the alloy at the maximum temperature for between three hours and six hours; and quenching the titanium alloy, wherein the resulting titanium alloy has a microstructure including an acicular alpha phase of between 20% and 75% of the area of a micrograph of the microstructure taken at 250× magnification.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein:

FIG. 4 is a photograph of the recrystallized microstructure of Ti-6Al-4V treated in accordance with the method described herein, taken under 250× magnification;

FIG. 5 is a photograph of the recrystallized microstructure of Ti-6Al-4V thermally treated at 1725° F. (940.6° C.) for 3 hours followed by argon quench, taken under 250× magnification;

FIG. 6 is a photograph of the recrystallized microstructure of Ti-6Al-4V thermally treated at 1725° F. (940.6° C.) for 4 hours followed by argon quench, taken under 250× magnification;

FIG. 7 is a photograph of the recrystallized microstructure of Ti-6Al-4V thermally treated at 1725° F. (940.6° C.) for 5 hours followed by argon quench, taken under 250× magnification;

FIG. 8 is a photograph of the recrystallized microstructure of Ti-6Al-4V thermally treated at 1725° F. (940.6° C.) for 6 hours followed by argon quench, taken under 250× magnification;

The exemplifications set out herein illustrate preferred embodiments of the invention and such exemplifications are not to be construed as limiting the scope of the invention in any manner.

DETAILED DESCRIPTION

The present invention provides a method for modifying the microstructure of titanium alloys for use in the manufacture of orthopedic prostheses, and orthopedic prostheses made from such method. Although the present invention is described below and in the following Examples in the context of the particular titanium alloy Ti-6Al-4V, the present invention is more generally applicable to alpha/beta titanium alloys in general and the teachings of the present method may be utilized with the following alpha/beta titanium alloys: Ti-10-2Fe-3Al, Ti-3Al-2.5V, Ti-5Al-2Sn-2Zr-4Mo-4Cr, Ti-6Al-2Sn-2Zr-2Mo-2Cr-0.25Si, Ti-6Al-2Sn-4Zr-6Mo, Ti-6Al-4V ELI, Ti-6Al-6V-2Sn-0.75Cu, Ti-7Al-4Mo, Ti-6Al-7Nb, and Ti-8Mn, for example.

Figure 1:
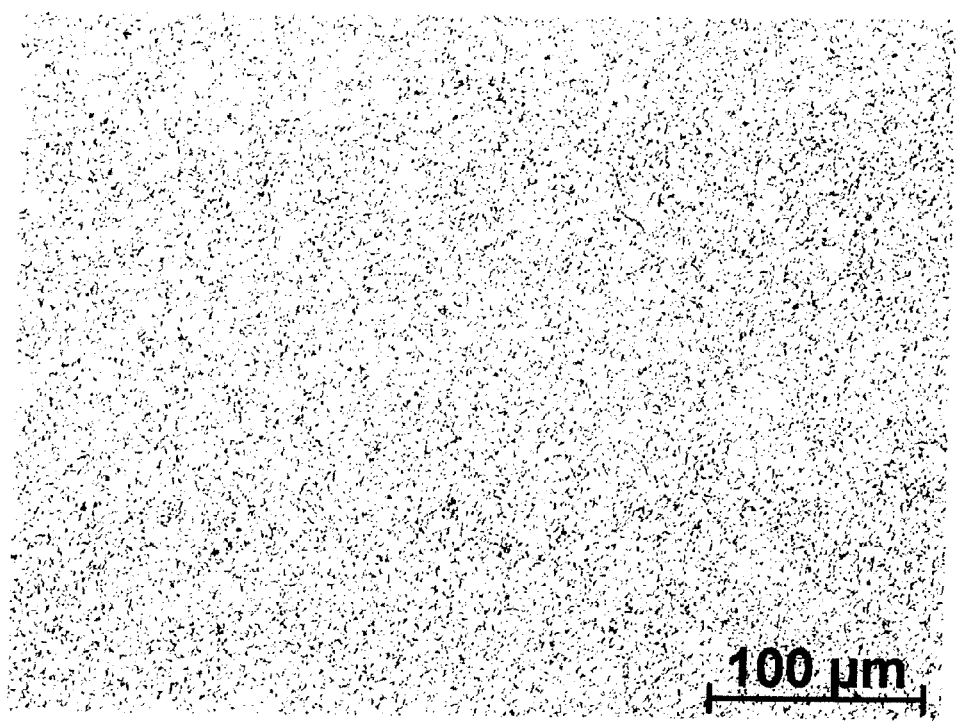
FIG. 1 is a photograph of the microstructure of mill annealed Ti-6Al-4V taken under 250× magnification.
Figure 2:
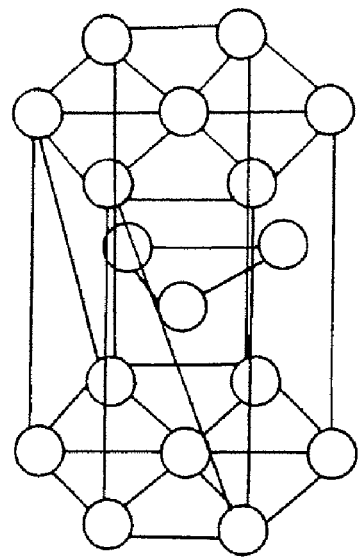
FIG. 2 is a diagram of a hexagonal close packed crystal structure.
Figure 3:
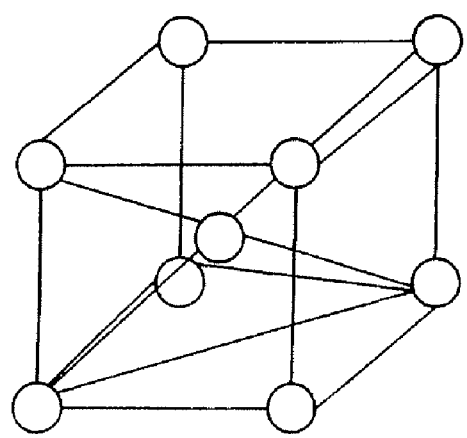
FIG. 3 is a diagram of a body centered cubic crystal structure.

Ti-6Al-4V is a titanium alloy used to manufacture orthopedic prosthesis and is readily available from numerous commercial sources. Stock Ti-6Al-4V alloy is typically received in mill annealed condition in which the alloy has a fine grained alpha-beta microstructure, shown in FIG. 1. In this condition, the alpha phase has a hexagonal close packed crystal structure, shown in FIG. 2, and the beta phase has a body centered cubic crystal structure, shown in FIG. 3. The melting point for mill annealed Ti-6Al-4V is approximately between 2420° F. (1327° C.) and 3020° F. (1660° C.) and the beta-transus temperature is approximately between 1777° F. (969.4° C.) and 1813° F. (989.4° C.). The beta-transus temperature is the temperature above which the microstructure is comprised entirely of the beta phase. Additionally, the recrystallization temperature of mill annealed Ti-6Al-4V is approximately 1695° F. (923.9° C.).

By modifying the microstructure of Ti-6Al-4V, the physical properties of the material can be correspondingly altered. Utilizing the present method, described below, the microstructure of Ti-6Al-4V is modified to form an equiaxed alpha phase (which appears as the lighter areas in FIGS. 4-8) and an acicular or plate-like alpha phase in the beta matrix (which appears as the darker areas in FIGS. 4-8). Both the equiaxed alpha phase and the acicular alpha phase have a hexagonal close packed crystal structure, shown in FIG. 2. However, respective distances between corresponding atoms in the equiaxed alpha phase and the acicular alpha phase may vary, resulting in the difference in appearance between the two phases. The acicular or plate-like alpha phase is formed by nucleation and growth from the transformation of the beta phase component in the mill annealed Ti-6Al-4V. As shown in FIG. 4, the acicular alpha phase appears as a basket-weave structure. Each individual grain of acicular alpha phase material may include one or more like-oriented regions which together comprise a colony. The colonies, in further combination, comprise the resultant basket-weave structure. As discussed in detail below, Ti-6Al-4V subjected to the present method has a much larger acicular alpha phase composition and a greater fretting fatigue resistance than mill annealed Ti-6Al-4V.

While the exact mechanism by which titanium alloy or prostheses made in accordance with the present method exhibit increased fretting fatigue resistance is not specifically understood at present, the increased fretting fatigue resistance is thought to result from the increased acicular alpha phase composition. In particular, it is thought that the modified microstructure may delay crack nucleation and early crack propagation, while the acicular alpha phase may work as a crack arrestor, causing an individual crack to deviate from its preferred path and to follow a path between the acicular alpha grains rather than an alpha-beta interface present in the mill annealed Ti-6Al-4V. When a crack makes an abrupt change in path, the matrix surrounding the crack must also accommodate the changed direction. This may create a larger fracture surface area within the material during crack propagation, allowing the material to absorb more energy before fracture, and require additional energy inputs to reinitiate the arrested crack. Therefore, crack arresting and fracture surface area maximization enhance the crack tolerance capacity, i.e., the ability of a material to accept crack formation without failure, and increase the energy absorption ability of the material, which are indicative of the material's overall toughness and resistance to fretting fatigue failure. Therefore, a material having a microstructure with a percentage of acicular alpha phase structure within a specified range may have an increased fretting fatigue resistance.

Figure 9:
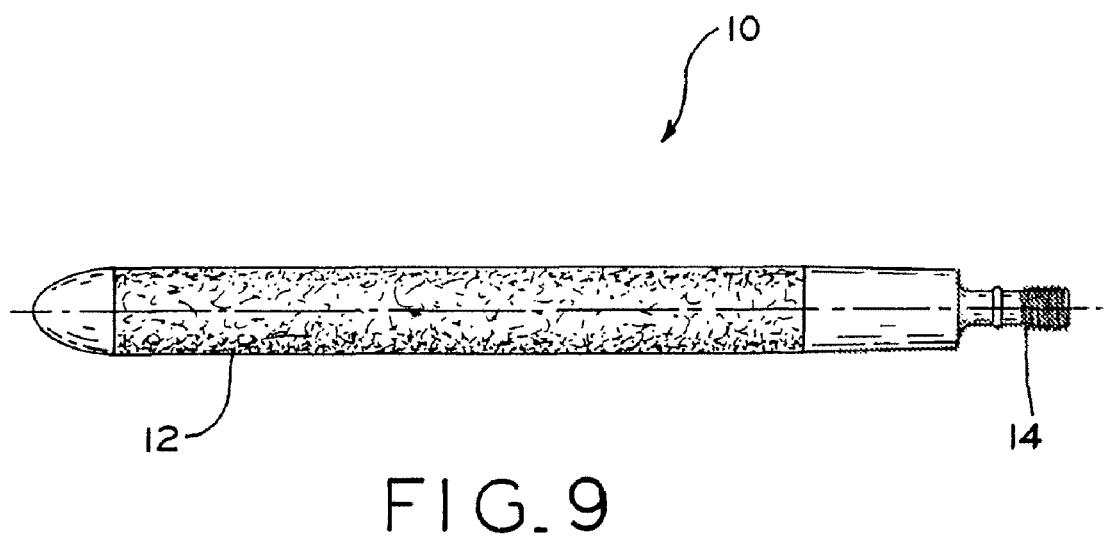
FIG. 9 is a perspective view of a hip stem made in accordance with the method of the present invention.

An exemplary method of modifying the microstructure of titanium alloy is hereafter described with reference to Ti-6Al-4V and FIGS. 9-11. First, referring to Steps 20 and 40 of FIGS. 10 and 11, respectively, a mill annealed Ti-6Al-4V is received. Referring to Step 42 of FIG. 11, in one exemplary embodiment, the titanium alloy is then machined to form the titanium alloy into an orthopedic prosthesis, such as femoral stem 10 of FIG. 9. Femoral stem 10 is one component of a modular proximal femoral prosthesis and includes body 12 and connection mechanism 14. Body 12 is configured for implantation within the intramedullary canal of the femur, while connection mechanism 14 is configured for securement to another component, such as a femoral neck (not shown), of the modular proximal femoral prosthesis. While depicted and described herein as femoral stem 10, the present invention may be used to form any orthopedic prosthesis formed from a titanium alloy, such as an acetabular cup, a tibial component, another distal femoral component, a glenoid component, or a humeral component, for example. Additionally, while the term "machining" and/or "machined" is used to refer to the process for creating the orthopedic implant, the terms "machining" and "machined" are inclusive any process used to create the final dimensions of the orthopedic implant, such as net shape molding.

Figure 10:
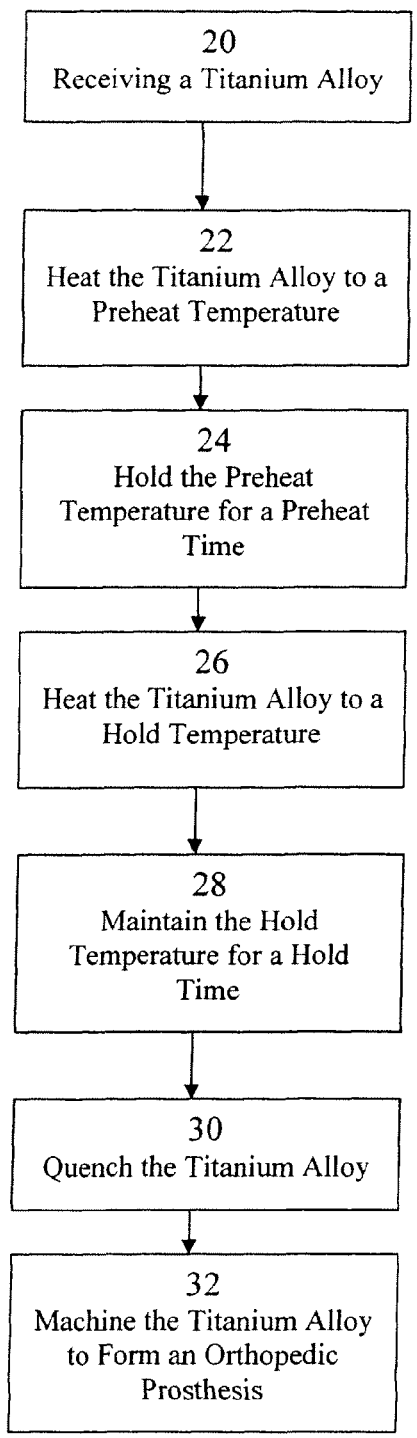
FIG. 10 is a flowchart depicting an exemplary process for making an orthopedic prosthesis according to the present invention.
Figure 11:
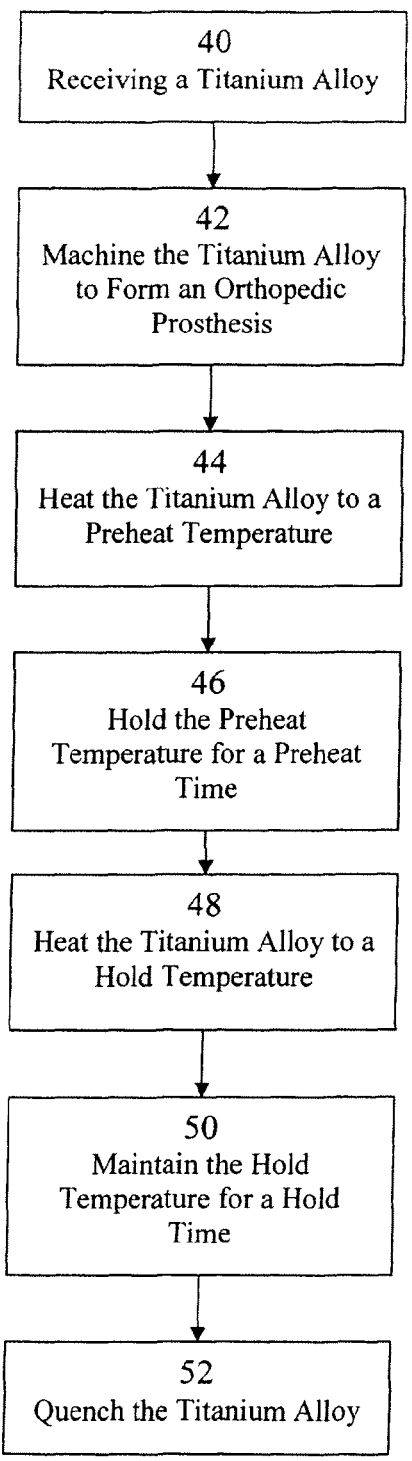
FIG. 11 is a flowchart depicting another exemplary process for making an orthopedic prosthesis according to the present invention.

Referring to FIGS. 10 and 11, the mill annealed Ti-6Al-4V and/or orthopedic prosthesis formed therefrom is then subjected to thermal treatment, i.e., a recrystallization heat treatment, in a vacuum furnace. Additionally, while the furnace of the exemplary method and the Examples contained hereinbelow is described as a vacuum furnace, any furnace capable of maintaining an inert atmosphere may be used. In the vacuum furnace, the temperature of the Ti-6Al-4V is raised at Steps 26, 48 to a predetermined hold temperature, which may be, for example, as low as 1675° F. (912.8° C.), 1700° F. (927° C.), or 1725° F. (941° C.), or as high as 1750° F. (954° C.), 1775° F. (968.3° C.), or 1800° F. (982° C.). Additionally, the temperature may be temporarily raised at Steps 22, 44 to a pre-hold temperature below the hold temperature and maintained at Steps 24, 46 for a short, pre-hold time, which may be as short as 2 minutes, 5 minutes, or 10 minutes, or as long as 15 minutes, 20 minutes, or 30 minutes, for example, to allow for homogenization of the alloy before being raised to the hold temperature. Homogenization ensures that the heat has been equally distributed throughout the alloy and that the entire mass of the alloy has reached the desired temperature. The hold temperature of the vacuum furnace is then held at Steps 28, 50 for a predetermined hold time which may be as short as 2 hours, 3 hours, or 4 hours, or as long as 6 hours, 7 hours or 8 hours, for example.

28 Following the expiration of the hold time, the Ti-6Al-4V is argon quenched at Steps 30, 52 of FIGS. 10 and 11. While an argon quench is used in the exemplary method and the Examples contained hereinbelow, it should be understood that the present method can utilize other substantially inert or inert gases, such as, for example, any of the elements in Group VIII of the periodic table and nitrogen, and liquids, such as liquid nitrogen, capable of rapidly cooling the heated titanium alloy. In one embodiment, the argon quench is performed by flooding the furnace with argon gas, which surrounds the alloy therein. The argon gas has an approximate temperature between −100° F. (−73° C.) and −125° F. (−87.2° C.). In another embodiment, a water quench is performed by submerging the alloy in water. In this embodiment, the outer surface of the alloy may be oxidized, wherein the alloy may be further subjected to a milling process to remove the oxidized layer. Referring to Step 32 of FIG. 10, in one exemplary embodiment, after the microstructure of the Ti-6Al-4V has been modified, the Ti-6Al-4V is then machined to form an orthopedic prosthesis, such as femoral stem 10 of FIG. 9.

In one embodiment, as depicted in FIGS. 3, 4, 5, and 6, the resulting microstructure of the Ti-6Al-4V includes an acicular alpha phase comprising the above discussed basket-weave structure in concentrations ranging between 30% and 55%. However, the acicular alpha phase concentrations may be as low as 20%, 30%, or 40%, or as high as 50%, 60%, or 75%. As used herein, the percentage of acicular alpha phase concentration is the estimated percentage of the total area of a micrograph of an alloy's microstructure at 250× magnification which is comprised of the acicular alpha phase.

EXAMPLES

The following Examples are presented to illustrate the invention, which is not to be considered as limited thereto. The following abbreviations are used in the Examples:

TABLE 1

| Abbreviations | |
|---|---|
| Abbreviation | Full Word |
| F | Fahrenheit |
| ° | degree |
| Hz | Hertz |
| N | Newton |
| Rc | C-Scale of Rockwell Hardness |

Example 1

Fretting Fatigue, Hardness, and Fatigue Strength Tests of Modified Microstructure Mill annealed Ti-6Al-4V was formed into ten complete, modular hip stems each having a mid-stem Morse taper. Each of the modular components that included the male portion of the Morse taper were subjected to thermal treatment. The individual modular components were placed in a Model H26 vacuum furnace, manufactured by Vacuum Furnace Systems Corporation of Souderton, Pa., and the temperature was raised at 25° F. (14° C.)/minute to 1000° F. (538° C.). At 1000° F. (538° C.), the temperature was held for 10 minutes to allow for homogenization, i.e., the equal distribution of heat throughout the components. After the expiration of 10 minutes, the temperature was raised at 25° F. (14° C.)/minute to 1500° F. (816° C.) where it was held for 15 minutes to further allow for homogenization. The temperature was then raised at 20° F. (11° C.)/minute until the temperature reached 1725° F. (940.6° C.), at which it was held for four hours. After the expiration of four hours, the Ti-6Al-4V components were argon quenched by injecting a stream of argon gas having an average temperature of −116.5° F. (−82.50° C.) directly into the furnace. The flow of argon gas into the furnace was stopped when the interior temperature of the furnace reaches approximately 72° F. (22° C.).

Following argon quenching, both thermal treated components and mill annealed components were subjected to fatigue tests. The modular hip stem components including the female portions of the Morse tapers were assembled on the tapers of the male components and potted in bone cement 0.25 inches below the mid-stem modular junction. Fatigue tests were conducted on specimens mounted in an anatomical orientation, i.e., inclined 15° in the medial/lateral direction, 10° in the anterior/posterior direction, with a 12° anteversion, in ambient conditions at a frequency of 10 Hz. Load was applied vertically using a MTS servohydraulic test machine, manufactured by MTS Systems Corporation of Minneapolis, Minn. The first specimen was cyclically loaded in a sinusoidal waveform for 10,000,000 cycles or until fracture, whichever occurred first. Upon completion of the initial test, the next specimen was tested at a higher or lower load depending on the results of the previous test. If the previous specimen had survived 10,000,000 cycles, the load was increased by approximately 10% of the previous load. Conversely, if the previous specimen experienced fracture, the load was decreased by approximately 10% of the previous load. The fretting fatigue strength was then determined for each microstructural condition by plotting the load versus the number of cycles curve on a semi-log scale. Fatigue tests were then repeated for two additional groups of specimens, each group containing ten individual specimens, with the groups being thermally treated for different time intervals.

The testing revealed that the fretting fatigue strength of the mill annealed male tapered components averaged 3113N, while the fretting fatigue strength of the thermal treated male tapered components averaged 4003N. This indicates that the thermal treated male tapered components had a fretting fatigue strength that was increased by approximately 30% over the mill annealed male tapered components at the mid-stem junction.

Further testing also revealed that the thermally treated specimens experienced a reduction in fatigue strength of between 8% and 10% in comparison to the mill annealed microstructural condition. This value was determined by subjecting ten specimens of each microstructural condition to constant stress amplitude fatigue tests on an MTS servohydraulic test machine, manufactured by MTS Systems Corporation of Minneapolis, Minn., at a frequency of 30 Hz in ambient air. The test method and analysis of the results were conducted in accordance with ASTM Test Method E 468-90, Standard Practice for Presentation of Constant Amplitude Fatigue Tests Results for Metallic Materials.

Additionally, the thermal treated male tapered components had a measured hardness of Rc 27.5 on the Rockwell Hardness Scale in comparison to a hardness of Rc 32 for the mill annealed male tapered components, a reduction of about Rc 4.5. The Rockwell Hardness tests were performed in accordance with ASTM E 18-93, Standard Test Methods for Rockwell Hardness and Rockwell Superficial Hardness of Metallic Materials.

Example 2

Effect of Varying Time and Temperature of the Thermal Treatment

Wrought mill annealed Ti-6Al-4V ELI titanium alloy bar (ASTM F-136-02A) was obtained from Supra Alloys, Inc. of Camarillo, Calif. The wrought alloy was 0.75 inch round bar stock which was cut into 5 inch long pieces. Each piece was subjected to a different thermal treatment cycle. A Model H26 vacuum furnace, manufactured by Vacuum Furnace Systems Corporation of Souderton, Pa., was used to raise the temperature of the test coupons at a rate of 25° F. (14° C.)/minute to the desired temperature with two intermittent holding periods for homogenization. The peak temperatures were selected from 1675° F. (913° C.) to 1800° F. (982° C.), as set forth in Table 2. All of the test coupons were heated for four hours. In parallel, test coupons were heated to 1725° F. (941° C.) and subjected to heating times varying between two hours and eight hours, as set forth in Table 3. After the desired heating, each coupon was argon quenched in a stream of argon gas having an average temperature of −116.5° F. (−82.5° C.).

TABLE 2

Specimens Thermally Treated for Four Hours at Varied Temperatures

| Specimen # | Temperature, ° F. (° C.) |
| --- | --- |
| 1 | 1675 (912.8) |
| 2 | 1700 (926.7) |
| 3 | 1725 (940.6) |
| 4 | 1750 (954.4) |
| 5 | 1775 (968.3) |
| 6 | 1800 (982.2) |

TABLE 3

Thermal treatment time for specimens held at 1725° F. (941° C.)

| Specimen # | Time, hours |
| --- | --- |
| 1 | 1 |
| 2 | 2 |
| 3 | 3 |
| 4 | 5 |
| 5 | 6 |
| 6 | 7 |
| 7 | 8 |

Upon heating and quenching, metallographic specimens were prepared from each test coupon using a Vibromet 2 vibratory polisher, manufactured by Buehler of Lake Bluff, Ill., and examined and analyzed using a Zeiss Axiovert 200 MAT microscope and Axiovisiokn image analysis software, both manufactured by Carl Zeiss Microimaging GmbH of Germany. The results of which are set forth in Table 4 below.

TABLE 4

Results of Metallographic Analysis

| Temperature, ° F. (° C.) | Time, hours | Acicular alpha phase structure, % |
| --- | --- | --- |
| 1675 (912.8) | 4 | 18 ± 5.4 |
| 1700 (926.7) | 4 | 24 ± 3.4 |
| 1725 (940.6) | 4 | 40 ± 2.5 |
| 1750 (954.4) | 4 | 28 ± 2.5 |
| 1775 (968.3) | 4 | 70 ± 5.3 |
| 1800 (982.2) | 4 | >90 or 0 |
| 1725 (940.6) | 1 | 17 ± 5.7 |
| 1725 (940.6) | 2 | 27 ± 3.6 |
| 1725 (940.6) | 3 | 48 ± 5.8 |
| 1725 (940.6) | 5 | 37 ± 3.5 |
| 1725 (940.6) | 6 | 30 ± 6.2 |
| 1725 (940.6) | 7 | 19 ± 4.1 |
| 1725 (940.6) | 8 | 0 |

The results indicate that acicular alpha phase may be obtained between 1675° F. and 1775° F. Additionally, the optimum holding time range for the thermal treatment step of improving the Ti-6Al-4V microstructure is between three and six hours. This time range provided acicular alpha phase in the range of 25% to 75%. Additionally, two time/temperature combinations resulted in extreme limits of acicular alpha phase microstructure. First, heating to a temperature of 1800° F. (982.2° C.) resulted in excess of 90% acicular alpha phase. This temperature is above the beta-transus temperature of the specific Ti-6Al-4V titanium alloy used and, therefore, initially resulted in complete conversion to the beta phase. However, during quenching the meta-stable beta phase underwent transformation to acicular alpha or transformed beta phase and the prior beta grain boundaries appeared decorated by acicular alpha phase. The acicular alpha phase obtained after heating above the beta transus temperature has a larger shape than the grains of alpha phase obtained by heating below the beta-transus temperature but above the alloy's recrystallization temperature, and may be less useful for medical implants. Additionally, the development of the acicular alpha phase along the prior beta grain boundaries increases the brittleness of the alloy and creates inconsistencies in the alloy's physical properties. On the other hand, if the quenching rates are rapid enough to suppress the nucleation and growth process, beta-phase may transform into martensite and, hence, the resulting microstructure would have no acicular alpha. Second, heating for 8 hours resulted in 0% acicular alpha phase because the amount of time the Ti-6Al-4V titanium alloy was exposed to 1725° F. (940.6° C.) caused the alpha phase to grow into globular shape.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for modifying the microstructure of titanium alloys, comprising the steps of:
   providing a mill annealed Ti-6Al-4V alloy having a fretting fatigue resistance and a fatigue strength;
   heating the titanium alloy to a maximum temperature above the titanium alloy's recrystallization temperature and below the titanium alloy's beta-transus temperature;

holding the titanium alloy at the maximum temperature for between three hours and five hours; and quenching the titanium alloy, wherein the fretting fatigue resistance of the resulting titanium alloy is increased and the fatigue strength of the resulting titanium alloy is decreased.

2. The method of claim 1, further comprising, after said quenching step, the additional step of machining the titanium alloy to form an orthopedic prosthesis.

3. The method of claim 1, wherein the titanium alloy of said heating step is a machined orthopedic prosthesis.

4. The method of claim 1, wherein said quenching step comprises exposure to an inert substance.

5. The method of claim 4, wherein said quenching step comprises exposure to an inert substance selected from the group consisting of helium, neon, argon, krypton, xenon, radon, and nitrogen.

6. The method of claim 1, wherein, after said quenching step, the resulting titanium alloy has a microstructure including an acicular alpha phase of between 20% and 75% of the area of a micrograph of the microstructure taken at 250× magnification.

7. A method for modifying the microstructure of titanium alloys, comprising the steps of:

providing a titanium alloy having a fretting fatigue resistance and a fatigue strength;

heating the titanium alloy to a maximum temperature above the titanium alloy's recrystallization temperature and below the titanium alloy's beta-transus temperature, wherein the maximum temperature of said heating step is between 1675° F. and 1775° F.;

holding the titanium alloy at the maximum temperature for between three hours and five hours; and quenching the titanium alloy, wherein the fretting fatigue resistance of the resulting titanium alloy is increased and the fatigue strength of the resulting titanium alloy is decreased.

8. The method of claim 7, further comprising, after said quenching step, the additional step of machining the titanium alloy to form an orthopedic prosthesis.

9. The method of claim 7, wherein the titanium alloy of said heating step is a machined orthopedic prosthesis.

10. The method of claim 7, wherein said quenching step comprises exposure to an inert substance.

11. The method of claim 10, wherein said quenching step comprises exposure to an inert substance selected from the group consisting of helium, neon, argon, krypton, xenon, radon, and nitrogen.

12. The method of claim 7, wherein, after said quenching step, the resulting titanium alloy has a microstructure including an acicular alpha phase of between 20% and 75% of the area of a micrograph of the microstructure taken at 250× magnification.

13. A method for modifying the microstructure of titanium alloys, comprising the steps of:

providing a titanium alloy having a fretting fatigue resistance and a fatigue strength;

heating the titanium alloy to a maximum temperature between 1675° F. and 1775° F.;

holding the titanium alloy at the maximum temperature for between three hours and five hours; and quenching the titanium alloy, wherein the resulting titanium alloy has a microstructure including an acicular alpha phase of between 20% and 75% of the area of a micrograph of the microstructure taken at 250× magnification and wherein the resulting titanium alloy has an increased fretting fatigue resistance and a decreased fatigue strength.

14. The method of claim 13, wherein said quenching step comprises exposure to an inert substance selected from the group consisting of helium, neon, argon, krypton, xenon, radon, and nitrogen.

15. The method of claim 13, wherein the titanium alloy of said heating step is a formed medical implant.

16. The method of claim 13, further comprising, after said quenching step, the additional step of machining the titanium alloy to form an orthopedic prosthesis.

* * * * *